United States Patent
Ragheb et al.

[11] Patent Number: 5,873,904
[45] Date of Patent: Feb. 23, 1999

[54] SILVER IMPLANTABLE MEDICAL DEVICE

[75] Inventors: Anthony O. Ragheb, West Lafayette; Brian L. Bates, Bloomington; Neal E. Fearnot, West Lafayette; Thomas A. Osborne, Bloomington; Thomas G. Kozma, West Lafayette, all of Ind.; Joseph W. Roberts, Minneapolis, Minn.; William D. Voorhees, III, West Lafayette, Ind.

[73] Assignees: Cook Incorporated, Bloomington; MED Institute, Inc., West Lafayette, both of Ind.

[21] Appl. No.: 803,843

[22] Filed: Feb. 24, 1997

Related U.S. Application Data

[63] Continuation-in-part of Ser. No. 645,646, May 16, 1996, which is a continuation-in-part of Ser. No. 484,532, Jun. 7, 1995, Pat. No. 5,609,629.

[51] Int. Cl.⁶ ........................................................ A61F 2/06
[52] U.S. Cl. ................................. 623/1; 623/11; 623/12; 604/53; 604/265
[58] Field of Search ................................. 623/1, 11, 12; 604/53, 265; 424/423, 426; 514/772.2, 772.3, 822; 523/112, 113

[56] References Cited

U.S. PATENT DOCUMENTS

| | | |
|---|---|---|
| 4,101,984 | 7/1978 | MacGregor . |
| 4,872,867 | 10/1989 | Joh . |
| 5,019,096 | 5/1991 | Fox, Jr. et al. ........................ 623/1 |
| 5,053,048 | 10/1991 | Pinchuk . |
| 5,059,166 | 10/1991 | Fischell et al. . |
| 5,067,491 | 11/1991 | Taylor, II et al. . |
| 5,108,424 | 4/1992 | Hoffman, Jr. et al. . |
| 5,112,457 | 5/1992 | Marchant . |
| 5,197,977 | 3/1993 | Hoffman, Jr. et al. . |
| 5,282,823 | 2/1994 | Schwartz et al. . |
| 5,298,255 | 3/1994 | Sawamoto et al. . |

(List continued on next page.)

FOREIGN PATENT DOCUMENTS

| | | |
|---|---|---|
| 0734721 | 10/1996 | European Pat. Off. . |
| 0747069 | 11/1996 | European Pat. Off. . |
| 1307055 | 2/1973 | United Kingdom . |
| 8911500 | 11/1989 | WIPO . |

OTHER PUBLICATIONS

Sushil Sheth, Vishva Dev, Harvey Jacobs, James S. Forrester, Frank Litvack, Neal L. Eigler, Prevention of Subacute Stent Thrombosis by Polymer–Polyethylene Oxide–Heparin Coating in the Rabbit Carotid Artery, Feb. 1995, JACC, 1001–1029.

R.D. Falb, G.A. Grode, M.T. Takahashi and R.I. Leininger, Characteristics of Heparinized Surfaces, Oct. 11, 1968, Interaction of Liquids at Solid Substrates.

Photodynamic therapy Application Approved, Feb. 15, 1996, Biomedical Technology Information Service.

(List continued on next page.)

*Primary Examiner*—Mickey Yu
*Assistant Examiner*—Francis K. Cuddihy
*Attorney, Agent, or Firm*—Richard J. Godlewski

[57] ABSTRACT

A silver implantable medical device 29 includes a structure 12 adapted for introduction into the vascular system, esophagus, trachea, colon, biliary tract, or urinary tract; at least one layer 18 of a bioactive material posited on one surface of structure 12; and at least one porous layer 20 posited over the bioactive material layer 18 posited on one surface of structure (12) and the bioactive-material-free surface. Also included is a layer or impregnation of silver 45. Preferably, the structure 12 is a coronary stent. The porous layer 20 is comprised of a polymer applied preferably by vapor or plasma deposition and provides a controlled release of the bioactive material. It is particularly preferred that the polymer is a polyamide, parylene or a parylene derivative, which is deposited without solvents, heat or catalysts, merely by condensation of a monomer vapor. Silver is included as a base material, coating or included in a carrier, drug, medicant material utilized with the implantable stent.

28 Claims, 8 Drawing Sheets

U.S. PATENT DOCUMENTS

| | | |
|---|---|---|
| 5,304,121 | 4/1994 | Sahatjian . |
| 5,314,688 | 5/1994 | Kauffman et al. . |
| 5,342,348 | 8/1994 | Kaplan . |
| 5,344,411 | 9/1994 | Domb et al. . |
| 5,344,444 | 9/1994 | Glastra . |
| 5,348,873 | 9/1994 | Matsuda et al. . |
| 5,356,433 | 10/1994 | Rowland et al. . |
| 5,380,299 | 1/1995 | Fearnot et al. . |
| 5,383,927 | 1/1995 | DeGoicoechea . |
| 5,383,928 | 1/1995 | Scott et al. . |
| 5,419,760 | 5/1995 | Narciso, Jr. . |
| 5,443,458 | 8/1995 | Eury . |
| 5,447,724 | 9/1995 | Helmus et al. . |
| 5,449,382 | 9/1995 | Dayton . |
| 5,455,040 | 10/1995 | Marchant . |
| 5,457,113 | 10/1995 | Cullinan et al. . |
| 5,464,450 | 11/1995 | Buscemi et al. . |
| 5,464,650 | 11/1995 | Berg et al. . |
| 5,554,181 | 9/1996 | Das ............ 623/1 |

OTHER PUBLICATIONS

Bruce Humphrey, Using Parylene for Medical Substrate Coating, Jan./Feb. 1996 Medical Plastics and Biomaterials.

LEXPAT KWIC site printout for U.S. Patent No. 5,070,117.

LEXPAT KWIC site printout for U.S. Patent No. 5,194,303.

Webster's New World Dictionary, Third College Edition, Fourth printing, 1989, p. 1053.

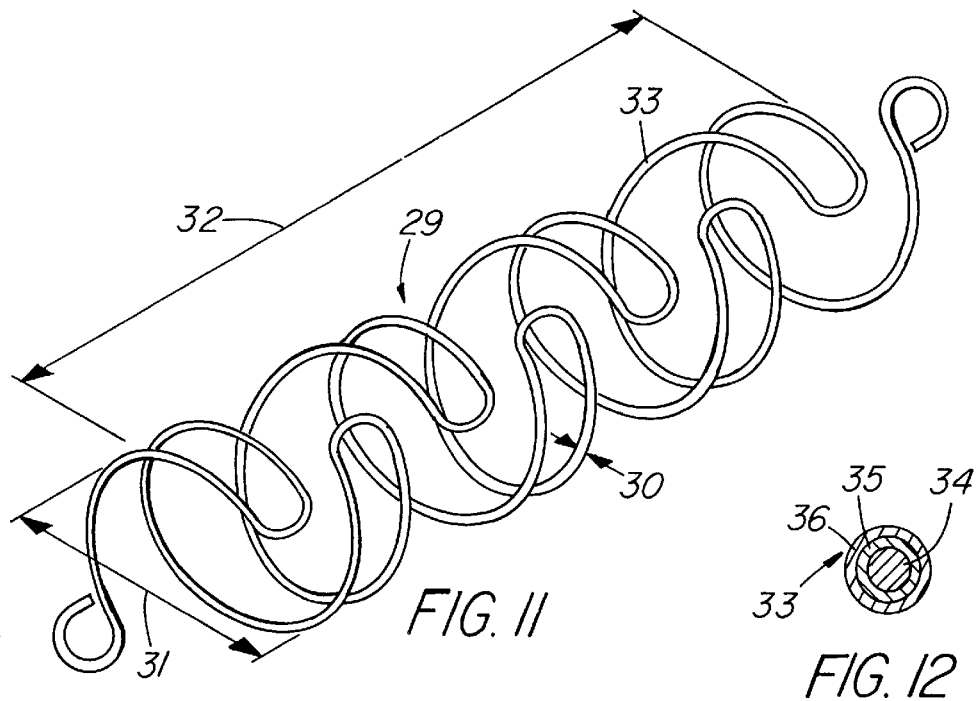
FIG. 11
FIG. 12
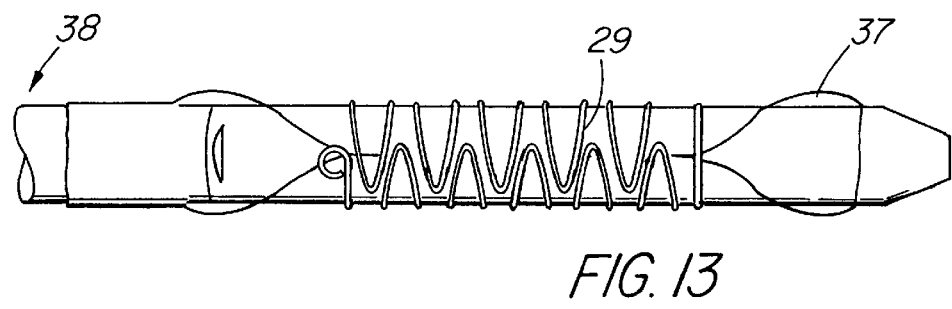
FIG. 13
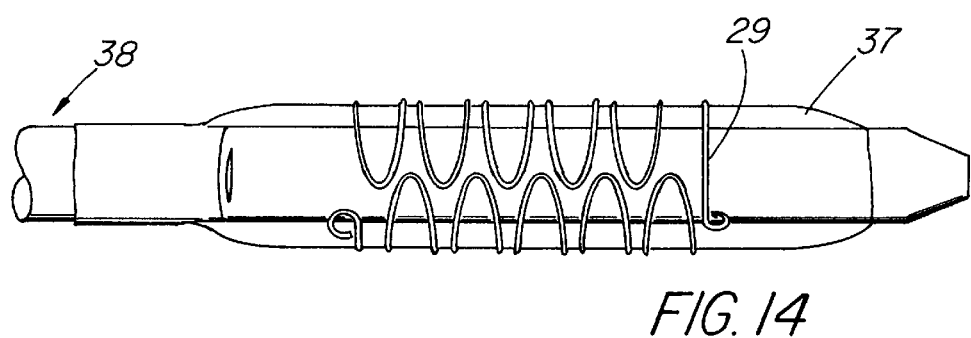
FIG. 14

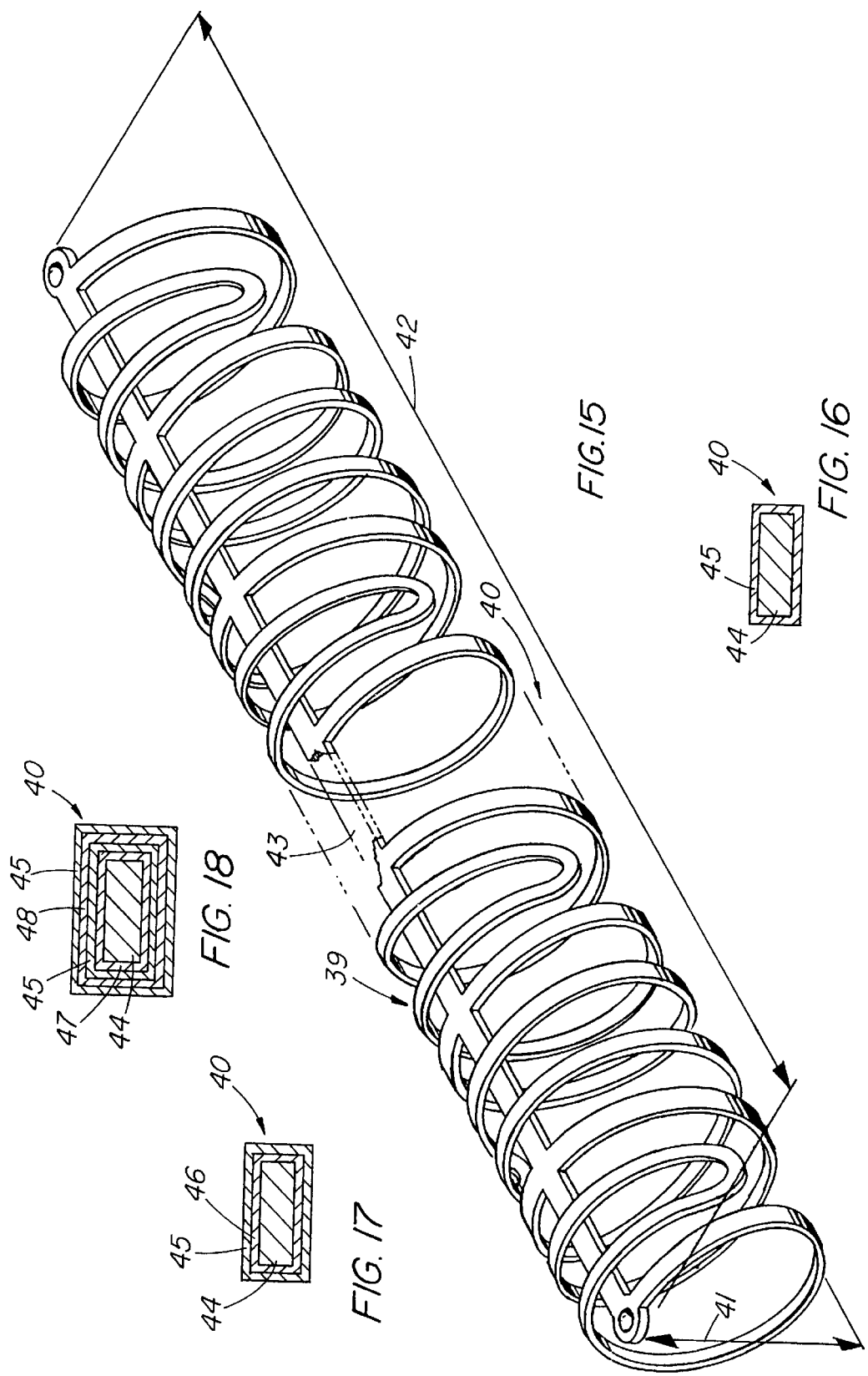

SILVER IMPLANTABLE MEDICAL DEVICE

CROSS-REFERENCE TO RELATED COPENDING APPLICATIONS

This application is a continuation-in-part of copending application Ser. No. 08/645,646, pending, filed on May 16, 1996 which is a continuation-in-part of application Ser. No. 08/484,532 filed Jun. 7, 1995, now U.S. Pat No. 5,609,629.

TECHNICAL FIELD

This invention relates generally to human and veterinary medical devices, and, particularly, to implantable medical devices with or without incorporating drugs or other bioactive agents and, more particularly, to an implantable device including silver with or without incorporating drugs or other bioactive agents.

BACKGROUND OF THE INVENTION

It has become common to treat a variety of medical conditions by introducing an implantable medical device partly or completely into the esophagus, trachea, colon, biliary tract, urinary tract, vascular system or other location within a human or veterinary patient. For introduction of a device such as a stent, a catheter, a balloon, a wire guide, a cannula, or the like. However, when such a device is introduced into and manipulated through the vascular system, the blood vessel walls can be disturbed or injured. Clot formation or thrombosis often results at the injured site, causing stenosis or occlusion of the blood vessel. Moreover, if the medical device is left within the patient for an extended period of time, thrombus often forms on the device itself, again causing stenosis or occlusion. As a result, the patient is placed at risk of a variety of complications, including heart attack, pulmonary embolism, and stroke. Thus, the use of such a medical device can entail the risk of precisely the problems that its use was intended to ameliorate.

Another way in which blood vessels undergo stenosis is through disease. Probably the most common disease causing stenosis of blood vessels is atherosclerosis. Atherosclerosis is a condition which commonly affects the coronary arteries, the aorta, the iliofemoral arteries and the carotid arteries. Atherosclerotic plaques of lipids, fibroblasts, and fibrin proliferate and cause obstruction of an artery or arteries. As the obstruction increases, a critical level of stenosis is reached, to the point where the flow of blood past the obstruction is insufficient to meet the metabolic needs of the tissue distal to (downstream of) the obstruction. The result is ischemia.

Many medical devices and therapeutic methods are known for the treatment of atherosclerotic disease. One particularly useful therapy for certain atherosclerotic lesions is percutaneous transluminal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic) directly into the arterial wall at the time of angioplasty could reduce the incidence of thrombotic acute closure, but the results of attempts to do so have been mixed.

A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling." It has similarly been postulated that the delivery of appropriate agents directly into the arterial wall could interrupt the cellular and/or remodeling events leading to restenosis. However, like the attempts to prevent thrombotic acute closure, the results of attempts to prevent restenosis in this manner have been mixed.

Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae and other devices inserted into the esophagus, trachea, colon, biliary tract, urinary tract and other locations in the body, or with orthopedic devices, implants, or replacements. It would be desirable to develop devices and methods for reliably delivering suitable agents, drugs or bioactive materials directly into a body portion during or following a medical procedure, so as to treat or prevent such conditions and diseases, for example, to prevent abrupt closure and/or restenosis of a body portion such as a passage, lumen or blood vessel. As a particular example, it would be desirable to have devices and methods which can deliver an antithrombic or other medication to the region of a blood vessel which has been treated by PTA, or by another interventional technique such as atherectomy, laser ablation, or the like. It would also be desirable that such devices would deliver their agents over both the short term (that is, the initial hours and days after treatment) and the long term (the weeks and months after treatment). It would also be desirable to provide precise control over the delivery rate for the agents, drugs or bioactive materials, and to limit systemic exposure to them. This would be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. A wide variety of other therapies could be similarly improved. Of course, it would also be desirable to avoid degradation of the agent, drug or bioactive material during its incorporation on or into any such device.

When an angioplasty is performed in a vessel, the inner layers of the vessel can be split or torn as the vessel is expanded. Stents are then frequently employed to keep the vessel open after angioplasty and to hold the torn or damaged tissue out of the blood stream. The result is usually very good in the short term; however, after six months to one year after the initial procedure, the vessels frequently become narrow again. Studies into the reason for the restenosis in these cases have shown that the restenosis is primarily due to the proliferation of fibroblasts resulting from the healing process that takes place in the vessel after the angioplasty. This proliferation of fibroblasts results in the formation of new tissue commonly known as smooth muscle cell proliferation to create a new restriction to blood flow in the vessel.

Other problems experienced with the use of catheters, particularly catheters designed for urinary tract infections present a significant risk in patients with an in dwelling catheter. Although most of such infections are asymptomatic, they are sometimes serious and can result in prolonging the length of stay and increasing the cost of hospital care. Bacteria are believed to gain access to the catheterized bladder either by migration from the collection bag and/or catheter or by ascending the periurethral space outside the catheter. It has been found that by coating catheters with silver or silver oxide reduced the incidence of catheter associated bacteriuria. Silver is known to possess antibacterial properties and is used topically either as a metal or as silver salts. It is not absorbed to any great extent and the main problem associated with the metal is argyria, a general grey discoloration.

SUMMARY OF THE INVENTION

The foregoing problems are solved and a technical advance is achieved in an illustrative silver vascular stent or other silver implantable medical device that advantageously reduces if not minimizes the proliferation of fibroblasts and the incidents of restenosis in stented vessels. The silver containing vascular stents can be balloon expandable, self-expanding, or any combination thereof. The balloon expandable silver stent can be deployed at the same time an angioplasty procedure is performed, thus advantageously requiring only one medical procedure. A solid silver vascular stent lends itself well to use in balloon expandable stents because of the malleable nature of the silver. The balloon expandable silver stent can also be made from a base material with good mechanical properties for stenting that is coated with silver by any one of a number of processes. These processes include electroplating, electrostatic, electrolytic, ion beam deposition or implantation, sputtering, vacuum deposition or other known application processes over base stent metals such as stainless steel, tantalum, nickel titanium alloys such as nitinol, polymer or copolymer plastics, copper, zinc, platinum, silver or gold, etc. The silver coating (which is used generically to indicate the application or inclusion in silver in any of the above-referenced application processes) can be applied directly to the base material or to an intermediate coating such as parylene or other metallic coating, e.g., Ti and Pd. The vascular stent or implantable medical device can also be made entirely of silver. Experience with central venous access catheters that have a silver coating for anti-sepsis has shown that a coating of silver with only a 3,000 angstroms thickness is adequate to be effective.

Silver may be alloyed with other materials both in the base stent or device material and/or in the coating. As a preferred example, the addition of small amount of copper to silver will increase its tensile strength. Pure silver has a maximum tensile strength of about 56 Kpsi. 85% silver and 15% copper has a maximum tensile strength of about 91 Kpsi, whereas a mixture of 50% silver with 50% copper may have maximum tensile strength of over 200 Kpsi.

The silver may be used in conjunction with other drugs or medicaments on the stent such as Heparin, Taxol, Dexamethosone along with others here after described to further enhance the stents or medical device or implantable medical devices' antithrombogenic or antiproliferative ability. Both the balloon expandable stent as well as the self-expanding stent can be assembled and/or completely coated or tinned with a silver barring solder (for example, 70% silver, 15% copper, 15% zinc) which may provide or supplement the antiproliferative action.

The foregoing problems are solved and a technical advance is achieved in an illustrative vascular stent or other implantable medical device that provides a controlled release of an agent, drug or other bioactive material into the vascular or other system, or other location in the body, in which a stent or other device is positioned. Applicants have discovered that the degradation of an agent, a drug or a bioactive material applied to such a device may be avoided by covering the agent, drug or other bioactive material with a porous layer of a biocompatible polymer that is applied without the use of solvents, catalysts, heat or other chemicals or techniques, which would otherwise be likely to degrade or damage the agent, drug or material. Those biocompatible polymers may be applied preferably by vapor deposition or plasma deposition, and may polymerize and cure merely upon condensation from the vapor phase, or may be photolytically polymerizable and are expected to be useful for this purpose. However, it should be recognized that other coating techniques may also be employed.

In a first aspect, then, the present invention is directed in its simplest form to an implantable medical device comprising a structure adapted for introduction into the esophagus, trachea, colon, biliary tract, urinary tract, vascular system or other location in a human or veterinary patient, the structure being composed of a base material; at least one layer of a bioactive material posited on one surface of the structure or posited in wells, holes, grooves, slots and the like contained in the structure; and at least one porous layer posited over the bioactive material layer and the bioactive-material-free surface, the porous layer being composed of a polymer and having a thickness adequate to provide a controlled release of the bioactive material.

Preferably, when the device is intended for use in the vascular system, the bioactive material in the at least one layer is heparin or another antiplatelet or antithrombotic agent, or dexamethasone, dexamethasone acetate, dexamethasone sodium phosphate, or another dexamethasone derivative or anti-inflammatory steroid. Furthermore, a wide range of other bioactive materials can be employed, including, but not limited to, the following categories of agents: thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radio labeled agents. The major restriction is that the bioactive material must be able to withstand the coating techniques, for example, the vacuum employed during vapor deposition or plasma deposition of the at least one porous layer. In other words, the bioactive material must have a relatively low vapor pressure at the deposition temperature, typically, near or at room temperature.

The at least one porous layer is preferably composed of a polyamide, parylene or a parylene derivative applied by catalyst-free vapor deposition and is conveniently about 5,000 to 250,000 Å thick, which is adequate to provide a controlled release of the bioactive material. "Parylene" is both a generic name for a known group of polymers based on p-xylylene and made by vapor phase polymerization, and a name for the unsubstituted form of the polymer; the latter usage is employed herein. More particularly, parylene or a parylene derivative is created by first heating p-xylene or a suitable derivative at an appropriate temperature (for example, at about 950° C.) to produce the cyclic dimer di-p-xylylene (or a derivative thereof). The resultant solid may be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and allowed to condense on the desired object, for example, on the at least one layer of bioactive material. The resultant polymer has the repeating structure $-(CH_2C_6H_4CH_2)_n-$, with n equal to about 5,000, and a molecular weight in the range of 500,000.

As indicated, parylene and parylene derivative coatings applicable by vapor deposition are known for a variety of biomedical uses, and are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

The at least one porous layer may alternatively be applied by plasma deposition. Plasma is an ionized gas maintained under vacuum and excited by electrical energy, typically in the radiofrequency range. Because the gas is maintained under vacuum, the plasma deposition process occurs at or near room temperature. Plasma may be used to deposit polymers such as poly(ethylene oxide), poly(ethylene glycol), and poly(propylene oxide), as well as polymers of silicone, methane, tetrafluoroethylene (including TEFLON brand polymers), tetramethyldisiloxane, and others.

While the foregoing represents some preferred embodiments of the present invention, other polymer systems may also be employed, e.g., polymers derived from photopolymerizeable monomers. Also, other coating techniques may be utilized, e.g., dipping, spraying, and the like.

The device may include two or more layers of different bioactive materials atop the structure. However, for the purposes of the present invention, the same bioactive material will generally not be posited on the different surfaces of the device within the same layer. In other words, each surface of the device structure will carry a different bioactive material or materials except where the bioactive material is the innermost or outermost layer, e.g. heparin may form the innermost layer or the outermost layer or both. These additional layers may be placed directly atop one another or can be separated by additional porous polymer layers between each of them. Additionally, the layers of bioactive materials may comprise a mixture of different bioactive materials. The porous layers are also preferably composed of parylene or a parylene derivative. Advantageously, the two or more bioactive materials can have different solubilities, and the layer containing the less soluble bioactive material (for example, dexamethasone) is preferably posited above the layer containing the more soluble bioactive material (for example, heparin). Unexpectedly, this has been found to increase the in vitro release rate of some relatively less soluble materials such as dexamethasone, while simultaneously decreasing the release rate of some relatively more soluble materials such as heparin.

While the structure included in the device may be configured in a variety of ways, the structure is preferably configured as a vascular stent composed of a biocompatible metal such as stainless steel, nickel, silver, platinum, gold, titanium, tantalum, iridium, tungsten, Nitinol, Inconel, or the like. An additional substantially nonporous coating layer of parylene or a parylene derivative or other biocompatible polymer of about 50,000 to 500,000Å thick may be posited directly atop the vascular stent, beneath the at least one layer of bioactive material. The additional coating layer can merely be relatively less porous than the at least one porous layer, but preferably is substantially nonporous, that is, sufficiently nonporous to render the stent essentially impervious to blood during normal circumstances of use.

In a second aspect, the present invention is directed to a method of making an implantable medical device of the type disclosed above, in which the method comprises the steps of: depositing at least one layer of a bioactive material on one surface of the structure; and depositing at least one porous layer over the at least one bioactive material layer and the bioactive-material-free surface, the at least one porous layer being composed of a polymer and being of a thickness adequate to provide a controlled release of the bioactive material. Conveniently and in a preferred embodiment, the at least one porous layer is polymerized from a monomer vapor which is free of any solvent or polymerization catalyst, and cures by itself upon condensation, without any additional heating or curing aid (for example, visible or ultraviolet light). The at least one layer of the bioactive material may be deposited on the one surface of the structure by any convenient method such as dipping, rolling, brushing, spraying, electrostatic deposition, or the like.

Lastly, in a third aspect, the present invention is directed to an improvement in a method of medically treating a human or veterinary patient by the step of inserting an implantable medical device into the body of the patient, the device comprising a structure adapted for introduction into an applicable system of or location in the patient, and the structure being composed of a base material, in which the procedure comprises the preliminary steps of: depositing at least one layer of a bioactive material on one surface of the structure; and depositing at least one porous layer over the at least one bioactive material layer and the bioactive-material-free surface, the at least one porous layer being composed of a polymer having a thickness adequate to provide a controlled release of the bioactive material.

The device and methods of the present invention are useful in a wide variety of locations within a human or veterinary patient, such as in the esophagus, trachea, colon, biliary tract, urinary tract and vascular system, as well as for subdural and orthopedic devices, implants or replacements. They are particularly advantageous for reliably delivering suitable bioactive materials during or following an intravascular procedure, and find particular use in preventing abrupt closure and/or restenosis of a blood vessel. More particularly, they permit, for example, the delivery of an antithrombotic, an antiplatelet, an anti-inflammatory steroid, or another medication to the region of a blood vessel which has been opened by PTA. Likewise, it allows for the delivery of one bioactive material to, for example, the lumen of a blood vessel and another bioactive material to the vessel wall. The use of a porous polymer layer permits the release rate of a bioactive material to be carefully controlled over both the short and long terms.

These and other aspects of the present invention will be appreciated by those skilled in the art upon the reading and understanding of the specification.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 11 is a pictorial view of a balloon expandable vascular stent with silver included therein;

FIG. 12 is a cross-sectional view of the cylindrical wire of the stent of FIG. 11;

FIG. 13 is side view of the silver vascular stent of FIG. 11 in a collapsed condition on a balloon catheter;

FIG. 14 is a side view of the stent of FIG. 13 in an expanded condition on a balloon catheter;

FIG. 15 is a pictorial view of another embodiment of a silver endovascular stent etched from a sheet of a base material;

FIG. 16–18 depict various cross-sectional views with silver, carrier, drug, or medicant layers positioned on a base material of, for example, a waveform leg of the stent of FIG. 15;

DETAILED DESCRIPTION OF THE PREFERRED EMBODIMENTS

Figure 1:
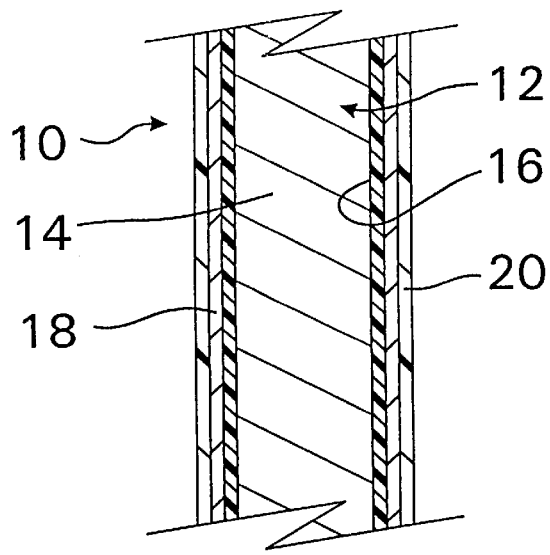
FIG. 1 is a cross-sectional view of a first preferred embodiment of the present invention.

With reference now to FIG. 1, an implantable medical device 10 in accordance with the present invention is shown and first comprises a structure 12 adapted for introduction into a human or veterinary patient. "Adapted" means that the structure 12 is shaped and sized for such introduction. For clarity, only a portion of the structure 12 is shown in FIG. 1.

By way of example, the structure 12 is configured as a vascular stent particularly adapted for insertion into the vascular system of the patient. However, this stent structure can be used in other systems and sites such as the esophagus, trachea, colon, biliary ducts, urethra and ureters, subdural among others. Indeed, the structure 12 can alternatively be configured as any conventional vascular or other medical device, and can include any of a variety of conventional stents or other adjuncts, such as helical wound strands, perforated cylinders, or the like. Moreover, because the problems addressed by the present invention arise with respect to those portions of the device actually positioned within the patient, the inserted structure 12 need not be an entire device, but can merely be that portion of a vascular or other device which is intended to be introduced into the patient. Accordingly, the structure 12 can be configured as at least one of, or any portion of, a catheter, a wire guide, a cannula, a stent, a vascular or other graft, a cardiac pacemaker lead or lead tip, a cardiac defibrillator lead or lead tip, a heart valve, or an orthopedic device, appliance, implant, or replacement. The structure 12 can also be configured as a combination of portions of any of these.

Most preferably, however, the structure 12 is configured as a vascular stent such as the commercially available Gianturco-Roubin FLEX-STENT coronary stent from Cook Incorporated, Bloomington, Indiana. Such stents are typically about 10 to about 60 mm in length and designed to expand to a diameter of about 2 to about 6 mm when inserted into the vascular system of the patient. The Gianturco-Roubin stent in particular is typically about 12 to about 25 mm in length and designed to expand to a diameter of about 2 to about 4 mm when so inserted.

These stent dimensions are, of course, applicable to exemplary stents employed in the coronary arteries. Structures such as stents or catheter portions intended to be employed at other sites in the patient, such as in the aorta, esophagus, trachea, colon, biliary tract, or urinary tract will have different dimensions more suited to such use. For example, aortic, esophageal, tracheal and colonic stents may have diameters up to about 25 mm and lengths about 100 mm or longer.

The structure 12 is composed of a base material 14 suitable for the intended use of the structure 12. The base material 14 is preferably biocompatible, although cytotoxic or other poisonous base materials may be employed if they are adequately isolated from the patient. Such incompatible materials may be useful in, for example, radiation treatments in which a radioactive material is positioned by catheter in or close to the specific tissues to be treated. Under most circumstances, however, the base material 14 of the structure 12 should be biocompatible.

A variety of conventional materials can be employed as the base material 14. Some materials may be more useful for structures other than the coronary stent exemplifying the structure 12. The base material 14 may be either elastic or inelastic, depending upon the flexibility or elasticity of the polymer layers to be applied over it. The base material may be either biodegradable or non-biodegradable, and a variety of biodegradable polymers are known. Moreover, some biologic agents have sufficient strength to serve as the base material 14 of some useful structures 12, even if not especially useful in the exemplary coronary stent.

Accordingly, the base material 14 may include at least one of stainless steel, tantalum, titanium, nitinol, gold, platinum, Inconal, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel is particularly useful as the base material 14 when the structure 12 is configured as a vascular stent.

Of course, when the structure 12 is composed of a radiolucent material such as polypropylene, polyethylene, or others above, a conventional radiopaque coating may and preferably should be applied to it. The radiopaque coating provides a means for identifying the location of the structure 12 by X-ray or fluoroscopy during or after its introduction into the patient's vascular system.

With continued reference to FIG. 1, the vascular device 10 of the present invention next comprises at least one layer 18 of a bioactive material posited on one surface of the structure 12. For the purposes of the present invention, at least one bioactive material is posited on one surface of the structure 12, and the other surface will either contain no bioactive material or one or more different bioactive materials. In this manner, one or more bioactive materials or drugs may be delivered, for example, with a vascular stent, to the blood stream from the lumen surface of the stent, and a different treatment may be delivered on the vessel surface of the stent. A vast range of drugs, medicaments and materials may be employed as the bioactive material in the layer 18, so long as the selected material can survive exposure to the vacuum drawn during vapor deposition or plasma deposition. Particularly useful in the practice of the present invention are materials which prevent or ameliorate abrupt closure and restenosis of blood vessels previously opened by stenting surgery or other procedures. Thrombolytics (which dissolve, break up or disperse thrombi) and antithrombogenics (which interfere with or prevent the formation of thrombi) are especially useful bioactive materials when the structure 12 is a vascular stent. Particularly preferred thrombolytics are urokinase, streptokinase, and the tissue plasminogen activators. Particularly preferred antithrombogenics are heparin, hirudin, and the antiplatelets.

Urokinase is a plasminogen activating enzyme typically obtained from human kidney cell cultures. Urokinase catalyzes the conversion of plasminogen into the fibrinolytic plasmin, which breaks down fibrin thrombi.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi. Alternatively, heparin may be covalently bound to the outer layer of structure 12. Thus, heparin would form the outermost layer of structure 12 and would not be readily degraded enzymatically, and would remain active as a thrombin inhibitor.

Of course, bioactive materials having other functions can also be successfully delivered by the device 10 of the present invention. For example, an antiproliferative agent such as methotrexate will inhibit over-proliferation of smooth muscle cells and thus inhibit restenosis of the dilated segment of the blood vessel. The antiproliferative is desirably supplied for this purpose over a period of about four to six months. Additionally, localized delivery of an antiproliferative agent is also useful for the treatment of a variety of malignant conditions characterized by highly vascular growth. In such cases, the device 10 of the present invention could be placed in the arterial supply of the tumor to provide a means of delivering a relatively high dose of the antiproliferative agent directly to the tumor.

A vasodilator such as a calcium channel blocker or a nitrate will suppress vasospasm, which is common following angioplasty procedures. Vasospasm occurs as a response to injury of a blood vessel, and the tendency toward vasospasm decreases as the vessel heals. Accordingly, the vasodilator is desirably supplied over a period of about two to three weeks. Of course, trauma from angioplasty is not the only vessel injury which can cause vasospasm, and the device 10 may be introduced into vessels other than the coronary arteries, such as the aorta, carotid arteries, renal arteries, iliac arteries or peripheral arteries for the prevention of vasospasm in them.

A variety of other bioactive materials are particularly suitable for use when the structure 12 is configured as something other than a coronary stent. For example, an anti-cancer chemotherapeutic agent can be delivered by the device 10 to a localized tumor. More particularly, the device 10 can be placed in an artery supplying blood to the tumor or elsewhere to deliver a relatively high and prolonged dose of the agent directly to the tumor, while limiting systemic exposure and toxicity. The agent may be a curative, a pre-operative debulker reducing the size of the tumor, or a palliative which eases the symptoms of the disease. It should be noted that the bioactive material in the present invention is delivered across the device 10, and not by passage from an outside source through any lumen defined in the device 10, such as through a catheter employed for conventional chemotherapy. The bioactive material of the present invention may, of course, be released from the device 10 into any lumen defined in the device, or to tissue in contact with the device and that the lumen may carry some other agent to be delivered through it. For example, tamoxifen citrate, Taxol® or derivatives thereof, Proscar®, Hytrin®, or Eulexin® may be applied to the tissue-exposed surface of the device for delivery to a tumor located, for example in breast tissue or the prostate.

Dopamine or a dopamine agonist such as bromocriptine mesylate or pergolide mesylate is useful for the treatment of neurological disorders such as Parkinson's disease. The device 10 could be placed in the vascular supply of the thalamic substantia nigra for this purpose, or elsewhere, localizing treatment in the thalamus.

A wide range of other bioactive materials can be delivered by the device 10. Accordingly, it is preferred that the bioactive material contained in the layer 18 includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin® or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, Taxol® or the derivatives thereof, or other anti-cancer chemotherapeutic agents; dexamethasone, dexamethasone sodium phosphate, dexamethasone acetate or another dexamethasone derivative, or another antiinflammatory steroid or non-steroidal antiinflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radio labeled form or other radio labeled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs; Proscar®, Hytrin® or other agents for treating benign prostatic hyperplasia (BHP) or a mixture of any of these; and various forms of small intestine submucosa (SIS).

In a particularly preferred aspect, the layer of bioactive material contains preferably from about 0.01 mg to about 10 mg and more preferably from about 0.1 mg to about 4 mg of the bioactive material per cm$^2$ of the gross surface area of the structure. "Gross surface area" refers to the area calculated from the gross or overall extent of the structure, and not necessarily to the actual surface area of the particular shape or individual parts of the structure. In other terms, about 100 μg to about 300 μg of drug per 0.001 inch of coating thickness may be contained on the device surface. The total loading or amount of bioactive material that may be contained on the device may range from about 10 μg to about 1000 μg. This range will vary depending on the specific bioactive material or drug, method of application and the like.

When the structure 12 is configured as a vascular stent, however, particularly preferred materials for the bioactive material of the layer 18 are heparin, anti-inflammatory steroids including but not limited to dexamethasone and its derivatives, and mixtures of heparin and such steroids.

Still with reference to FIG. 1, the device 10 of the present invention also comprises at least one porous layer 20 posited over the layer 18 of bioactive material and the bioactive-material-free surface. The purpose of the porous layer 20 is to provide a controlled release of the bioactive material when the device 10 is positioned in the vascular system of a patient. The thickness, porosity and the like of the porous layer 20 is selected so as to provide such control.

More particularly, the porous layer 20 is composed of a polymer deposited on the bioactive material layer 18, preferably by vapor deposition. Plasma deposition may also be useful for this purpose. Preferably, the layer 20 is one that is polymerized from a vapor which is free of any solvent, catalysts or similar polymerization promoters. Also preferably, the polymer in the porous layer 20 is one which automatically polymerizes upon condensation from the vapor phase, without the action of any curative agent or activity such as heating, the application of visible or ultraviolet light, radiation, ultrasound, or the like. Most preferably, the polymer in the porous layer 20 is polyimide, parylene or a parylene derivative.

When first deposited, the parylene or parylene derivative is thought to form a network resembling a fibrous mesh, with relatively large pores. As more is deposited, the porous layer 20 not only becomes thicker, but it is believed that parylene or parylene derivative is also deposited in the previously formed pores, making the existing pores smaller. Careful and precise control over the deposition of the parylene or parylene derivative therefore permits close control over the release rate of material from the at least one layer 18 of bioactive material. It is for this reason that the bioactive material lies under the at least one porous layer 20, rather than being dispersed within or throughout it. The porous layer 20, however, also protects the bioactive material layer 18 during deployment of the device 10, for example, during insertion of the device 10 through a catheter and into the vascular system or elsewhere in the patient.

As shown in FIG. 1, the device 10 of the present invention can further comprise at least one additional coating layer 16 posited between the structure 12 and the at least one layer 18 of bioactive material. While the additional coating layer 16 can simply be a medical grade primer, the additional coating layer 16 is preferably composed of the same polymer as the at least one porous layer 20. However, the additional coating layer 16 is also preferably less porous than the at least one porous layer 20, and is more preferably substantially nonporous. "Substantially nonporous" means that the additional coating layer 16 is sufficiently impervious to prevent any appreciable interaction between the base material 14 of the structure 12 and the blood to which the device 10 will be exposed during use. The use of an additional coating layer 16 which is substantially nonporous would permit the use of a toxic or poisonous base material 14, as mentioned above. Even if the base material 14 of the structure 12 is biocompatible, however, it may be advantageous to isolate it from the blood by use of a substantially nonporous coating layer 16.

Other polymer systems that may find application within the scope of the invention include polymers derived from photopolymerizable monomers such as liquid monomers preferably having at least two cross linkable C—C (Carbon to Carbon) double bonds and being a non-gaseous addition polymerizable ethylenically unsaturated compound, having a boiling point above 100° C., at atmospheric pressure, a molecular weight of about 100–1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof. A few illustrative examples of such multi functional acrylates are ethylene glycol diacrylate, ethylene glycol dimethacrylate, trimethylolpropane triacrylate, trimethylolpropane trimethacrylate, pentaerythritol tetraacrylate or pentaerythritol tetramethacrylate, 1,6-hexanediol dimethacrylate, and diethyleneglycol dimethacrylate.

Also useful in some special instances are monoacrylates such as n-butyl-acrylate, n-butyl methacrylate, 2-ethylhexyl acrylate, lauryl-acrylate, and 2-hydroxy-propyl acrylate. Small quantities of amides of (meth)acrylic acid such as N-methylol methacrylamide butyl ether are also suitable, N-vinyl compounds such as N-vinyl pyrrolidone, vinyl esters of aliphatic monocarboxylic acids such as vinyl oleate, vinyl ethers of diols such as butanediol-1, 4-divinyl ether and allyl ether and allyl ester are also suitable. Also included would be other monomers such as the reaction products of di- or polyepoxides such as butanediol-1, 4-diglycidyl ether or bisphenol A diglycidyl ether with (meth)acrylic acid. The characteristics of the photopolymerizable liquid dispersing medium can be modified for the specific purpose by a suitable selection of monomers or mixtures thereof.

Other useful polymer systems include a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly (hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, poly(amino acids), cyanoacrylates, poly(trimethylene carbonate), poly(imino carbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

While plasma deposition and vapor phase deposition may be a preferred method for applying the various coatings on the stent surfaces, other techniques may be employed. For example, a polymer solution may be applied to the stent and the solvent allowed to evaporate, thereby leaving on the stent surface a coating of the polymer and the therapeutic substance. Typically, the solution can be applied to the stent by either spraying the solution onto the stent or immersing the stent in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

When the layer 18 of bioactive material contains a relatively soluble material such as heparin, and when the at least one porous layer 20 is composed of parylene or a parylene derivative, the at least one porous layer 20 is preferably about 5,000 to 250,000 Å thick, more preferably about 5,000 to 100,000 Å thick, and optimally about 50,000 Å thick. When the at least one additional coating layer 16 is composed of parylene or a parylene derivative, the at least one additional coating is preferably about 50,000 to 500,000 Å thick, more preferably about 100,000 to 500,000 Å thick, and optimally about 200,000 Å thick.

When the at least one layer 18 of bioactive material contains a relatively soluble material such as heparin, the at least one layer 18 preferably contains a total of about 0.1 to 4 mg of bioactive material per $cm^2$ of the gross surface area of the structure 12. This provides a release rate for the heparin (measured in vitro) which is desirably in the range of 0.1 to 0.5 mg/$cm^2$ per day, and preferably about 0.25 mg/$cm^2$ per day, under typical blood flows through vascular stents. It should be noted that the solubility of dexamethasone can be adjusted as desired, with or without the inclusion of heparin, by mixing it with one or more of its relatively more soluble derivatives, such as dexamethasone sodium phosphate.

Figure 2:
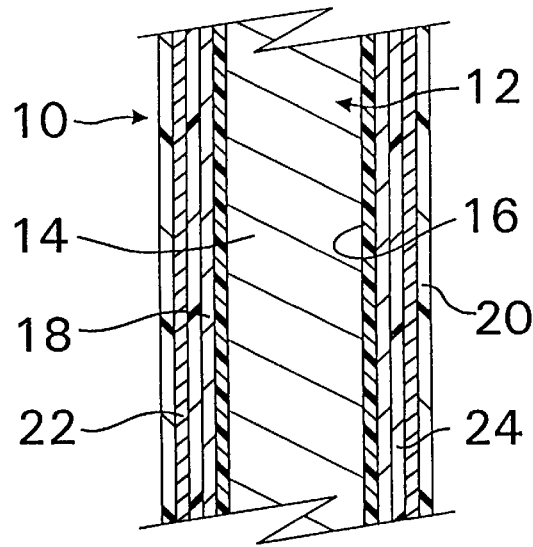
FIG. 2 is a cross-sectional view of another preferred embodiment of the present invention.

As shown in FIG. 2, the device 10 of the present invention is not limited to the inclusion of a single layer 18 of bioactive material. The device 10 can, for example, comprise a second layer 22 of a bioactive material posited over the structure 12. The bioactive material of the second layer 22 can be, but need not necessarily be, different from the bioactive material of the first bioactive material layer 18, only that they not be posited on the same surface of the device 10 without the intermediate porous layer 24. The use of different materials in the layers 18 and 22 allows the device 10 to perform more than a single therapeutic function.

Figure 8:
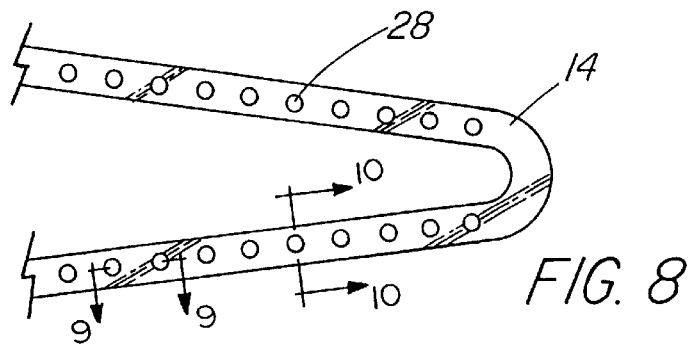
FIG. 8 is a partial, enlarged top view of FIG. 7.
Figure 9:
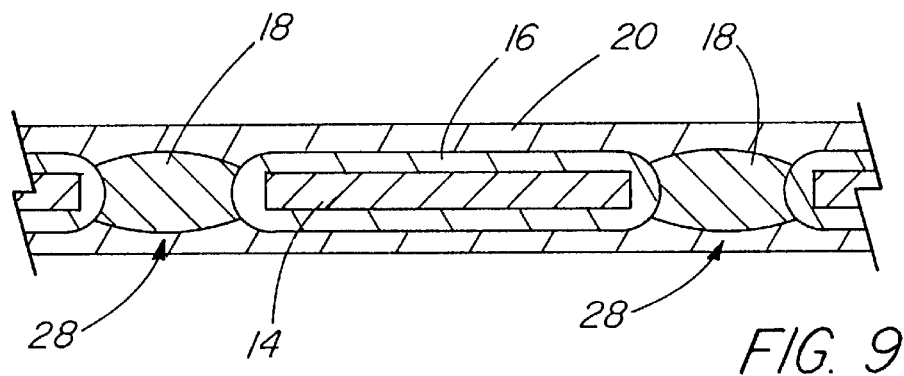
FIG. 9 is an enlarged, sectional view along lines 9—9 of FIG. 8.

The device 10 of the present invention can further comprise an additional porous layer 24 of the polymer posited between each of the layers 18 and 22 of bioactive material. It is reiterated that bioactive material 18 is on one surface of structure 12. The other surface may be free of bioactive material or may comprise one or more different bioactive materials. The additional porous layer 24 can give the bioactive materials in the layers 18 and 22 different release rates. Simultaneously, or alternatively, the device 10 may employ bioactive materials in the two layers 18 and 22 which are different from one another and have different solubilities. In such a case, it is advantageous and preferred to position the layer 22 containing the less soluble bioactive material above the layer 18 containing the more soluble bioactive material. Alternatively, the bioactive material 18 may be contained in holes, wells, slots and the like occurring within the stent surface as illustrated in FIGS. 8–10 and will further be discussed in greater detail.

For example, when the structure 12 of the device 10 is configured as a vascular stent, it is advantageous for the at least one layer 18 to contain relatively soluble heparin, and the second layer 22 to contain relatively less soluble dexamethasone. Unexpectedly, the heparin promotes the release of the dexamethasone, increasing its release rate many times over the release rate of dexamethasone in the absence of heparin. The release rate of the heparin is also lowered, somewhat less dramatically than the increase of the dexamethasone release rate. More particularly, when dexamethasone is disposed by itself beneath a porous parylene layer 20 dimensioned as disclosed above, its release rate is negligible; an adequate release rate is obtained only when the thickness of the porous layer 20 is reduced by a factor of ten or more. In contrast, when a layer 22 of dexamethasone is disposed over a layer 18 of heparin, and beneath a porous parylene layer 20 dimensioned as above, the dexamethasone may be released at a desirable rate of about 1 to 10 $\mu g/cm^2$ per day. Moreover, and even more unexpectedly, this increased release rate for the dexamethasone is thought to be maintained even after all of the heparin has been released from the layer 18.

The bioactive material layers 18 and/or 22 are applied to the device 10 independent of the application of the porous polymer layers 20 and/or 24. Any mixing of a bioactive material from the layers 18 and/or 22 into the porous layers 20 and/or 24, prior to introducing the device 10 into the vascular system of the patient, is unintentional and merely incidental. This gives significantly more control over the release rate of the bioactive material than the simple dispersal of a bioactive material in a polymeric layer.

Figure 3:
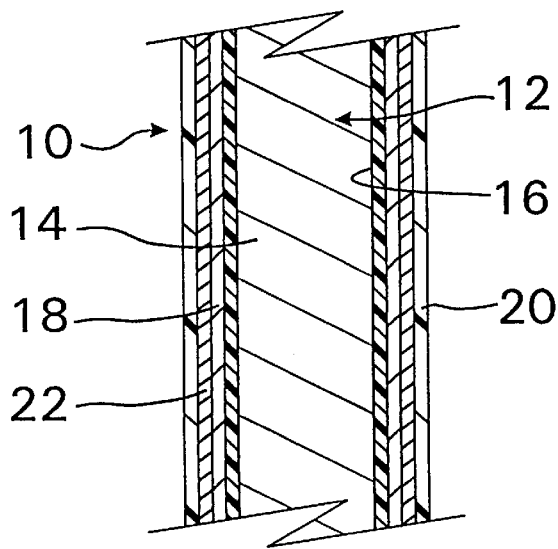
FIG. 3 is a cross-sectional view of yet another preferred embodiment of the present invention.

The device 10 need not include the additional porous layer 24 when two or more layers 18 and 22 of bioactive material are present. As shown in FIG. 3, the layers 18 and 22 do not have to be separated by a porous layer, but can instead lie directly against one another. It is still advantageous in this embodiment to position the layer 22 containing the relatively less soluble bioactive material above the layer 18 containing the relatively more soluble bioactive material.

Whether or not the additional porous layer 24 is present, it is preferred that the layers 18 and 22 contain about 0.05 to 2.0 mg of each of heparin and dexamethasone, respectively, per 1 $cm^2$ of the gross surface area of the structure 12. The total amount of bioactive material posited in the layers 18 and 22 over the structure 12 is thus preferably in the range of about 0.1 to 10 $mg/cm^2$.

Some dexamethasone derivatives, such as dexamethasone sodium phosphate, are substantially more soluble than dexamethasone itself. If a more soluble dexamethasone derivative is used as the bioactive material in the device 10 of the present invention, the thickness of the at least one porous layer 20 (and of the additional porous layer 24) may be adjusted accordingly.

The particular structure of the device 10 as disclosed may be adapted to specific uses in a variety of ways. For example, the device 10 may include further layers of the same or different bioactive materials. These additional layers of bioactive material may or may not be separated by additional porous layers, as convenient or desired. Alternatively, additional porous layers may separate only some of the additional layers of bioactive material. Moreover, one bioactive material may be placed on one portion of the structure 12 of the device 10, and another bioactive material placed on a different portion of the structure 12 of the device 10.

Figure 4:
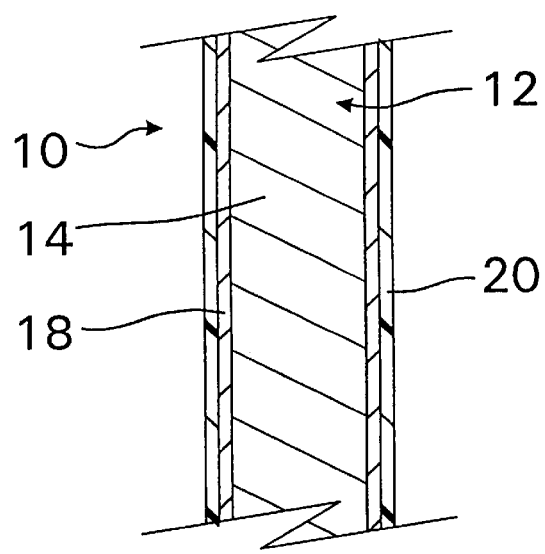
FIG. 4 is a cross-sectional view of a further preferred embodiment of the present invention.

Alternatively, the device 10 need not include the additional coating layer 16 at all. Such a configuration is shown in FIG. 4, in which the bioactive material layer 18 is posited directly atop the base material 14 of the structure 12. In such a case, it may be highly advantageous to surface process or surface activate the base material 14, to promote the deposition or adhesion of the bioactive material on the base material 14, especially before the depositing of the at least one porous layer 20. Surface processing and surface activation can also selectively alter the release rate of the bioactive material. Such processing can also be used to promote the deposition or adhesion of the additional coating layer 16, if present, on the base material 14. The additional coating layer 16 itself, or any second or additional porous layer 24 itself, can similarly be processed to promote the deposition or adhesion of the bioactive material layer 18, or to further control the release rate of the bioactive material.

Useful methods of surface processing can include any of a variety of such procedures, including: cleaning; physical modifications such as etching, drilling, cutting, or abrasion; and chemical modifications such as solvent treatment, the application of primer coatings, the application of surfactants, plasma treatment, ion bombardment and covalent bonding.

It has been found particularly advantageous to plasma treat the additional coating layer 16 (for example, of parylene) before depositing the bioactive material layer 18 atop it. The plasma treatment improves the adhesion of the bioactive material, increases the amount of bioactive material that can be deposited, and allows the bioactive material to be deposited in a more uniform layer. Indeed, it is very difficult to deposit a hygroscopic agent such as heparin on an unmodified parylene surface, which is hydrophobic and poorly wettable. However, plasma treatment renders the parylene surface wettable, allowing heparin to be easily deposited on it.

Any of the porous polymer layers 20 and 24 may also be surface processed by any of the methods mentioned above to alter the release rate of the bioactive material or materials, and/or otherwise improve the biocompatibility of the surface of the layers. For example, the application of an overcoat of polyethylene oxide, phosphatidylcholine or a covalently bound bioactive material, e.g., covalently attached heparin to the layers 20 and/or 24 could render the surface of the layers more blood compatible. Similarly, the plasma treatment or application of a hydrogel coating to the layers 20 and/or 24 could alter their surface energies, preferably providing surface energies in the range of 20 to 30 dyne/cm, thereby rendering their surfaces more biocompatible.

Figure 5:
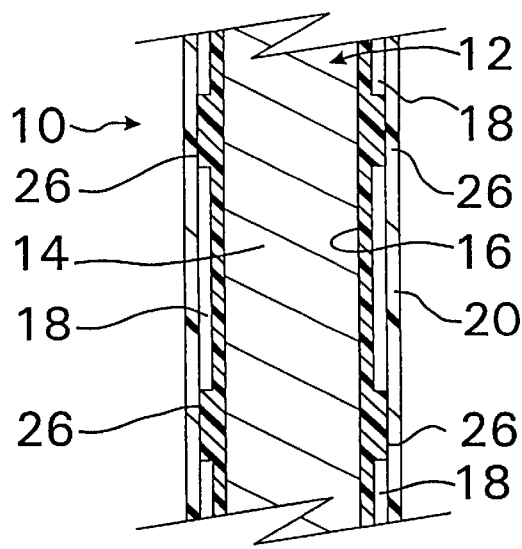
FIG. 5 is a cross-sectional view of an additional preferred embodiment of the present invention.

Referring now to FIG. 5, an embodiment of the device 10 is there shown in which a mechanical bond or connector 26 is provided between (a) any one of the porous layers 20 and 24, and (b) any or all of the other of the porous layers 20 and 24, the additional coating layer 16 and the base material 14. The connector 26 reliably secures the layers 16, 20 and/or 24 to each other, and or to the base material 14. The connector 26 lends structural integrity to the device 10, particularly after the bioactive material layer or layers 18 and/or 20 have been fully released into the patient.

For simplicity, the connector 26 is shown in FIG. 5 as a plurality of projections of the base material 14 securing a single porous layer 20 to the base material 14. The connector 26 may alternatively extend from the porous layer 20, through the bioactive material layer 18, and to the base material 14. In either case, a single layer 18 of bioactive material, divided into several segments by the connector 26, is posited between the porous layer 20 and the base material 14. The connectors can also function to partition the different bioactive agents into different regions of the device's surface.

The connector 26 may be provided in a variety of ways. For example, the connector 26 can be formed as a single piece with the base material 14 during its initial fabrication or molding into the structure 12. The connector 26 can instead be formed as a distinct element, such as a bridge, strut, pin or stud added to an existing structure 12. The connector 26 can also be formed as a built-up land, shoulder, plateau, pod or pan on the base material 14. Alternatively, a portion of the base material 14 between the desired locations of plural connectors 26 may be removed by etching, mechanical abrasion, or the like, and the bioactive material layer 18 deposited between them. The connector 26 can also be formed so as to extend downwards towards the base material 14, by wiping or etching away a portion of a previously applied bioactive material layer 18, and allowing the porous layer 20 to deposit by vapor deposition or plasma deposition directly on the bare portions of the base material 14. Other ways to expose a portion of the base material 14 to direct connection to the porous layer 20 will be evident to those skilled in this area.

Figure 7:
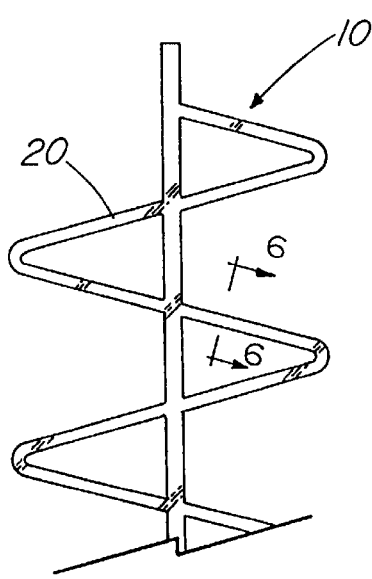
FIG. 7 is a cross-sectional view of an additional preferred embodiment of the present invention.
Figure 6A:
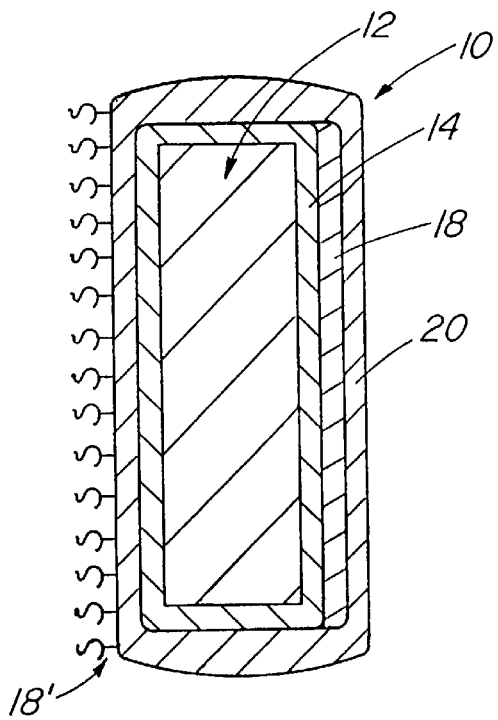
FIGS. 6A and 6B are cross-sectional views of an additional preferred embodiment of the present invention.
Figure 6B:
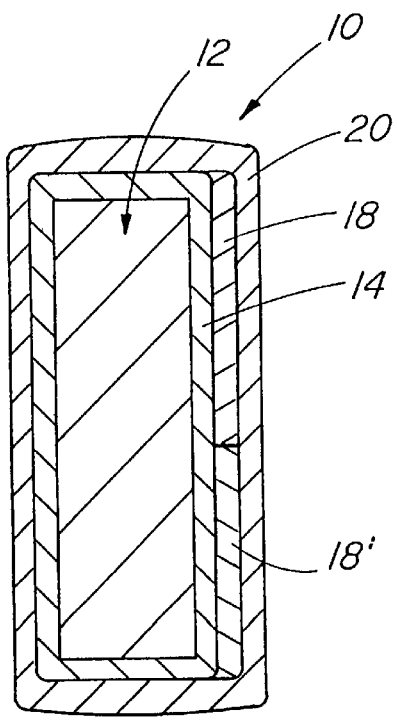

In another preferred embodiment, as illustrated in FIGS. 6A, 6B and 7, a bioactive material 18 is posited on the one surface of base material 14 making up structure 12 in FIG. 6A. FIG. 7 shows a stent 10 in its flat or planar state prior to being coiled and showing porous layer 20 applied to its outermost surface. FIGS. 6A and 6B are section views along line 6—6 of FIG. 7. The bioactive material 18 posited on the one surface of base material 14 in FIG. 6A may be a number of different therapeutic and/or diagnostic agents. For example, the device 10 may be a stent which is placed in the body of a patient near a tumor to deliver a chemotherapeutic agent, such as tamoxifen citrate or Taxol®, directly to the tumor. A porous layer 20 is posited over the bioactive material 18 to provide a smoother surface as well as a more controlled release of the bioactive material 18. As further illustrated in FIG. 6A, the opposite surface of the device may have, for example, heparin 18' covalently bonded to porous layer 20, particularly where this surface faces, for example, the lumen of a blood vessel, to provide antithrombotic effect and blood compatibility. It is pointed out, as has been discussed herein, a third but different bioactive material may be posited (not shown) on the opposite surface of base material 14 from the first bioactive material 18 and on the same side of base material 14 as the covalently bound heparin or any other bioactive material including other covalently bound bioactive materials and separated by porous layer 20. Such a bioactive material may be silver either posited on or impregnated in the surface matrix of porous layer 20. Such a bioactive material may be silver either posited on or impregnated in the surface matrix of porous layer 20.

A variation of the embodiment shown in FIG. 6A is illustrated in FIG. 6B, where two bioactive materials 18 and 18' are posited on the same surface of base material 14 of structure 12. A porous layer 20 may be deposited over the bioactive materials 18 and 18' as well as the bioactive-material-free surface of based material 14. This embodiment illustrates a situation where it may be desirable to deliver two agents to the tissue to which the particular surface of device 10 is exposed, e.g., an antiinflammatory agent and an antiviral agent. Moreover, the opposite surface of the device free of bioactive material is available for positing one or more bioactive materials or therapeutic agents, e.g., an antithrombotic agent or silver.

As has been previously discussed, multiple layers of bioactive materials and porous layers may be applied to the device 10 where the limiting factors become the total thickness of the device, the adhesion of multiple layers and the like.

Figure 10A:
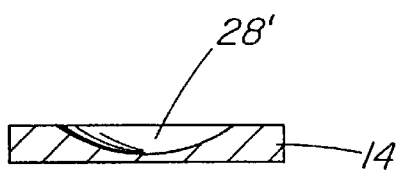
FIGS. 10A–10D are enlarged cross-sectional views along lines 10—10 of FIG. 8.
Figure 10C:
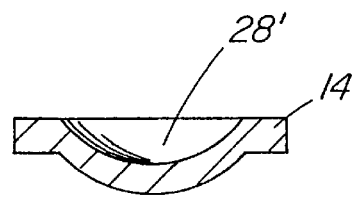
Figure 10B:
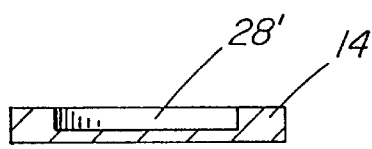
Figure 10D:

In still another embodiment of the present invention, the device of the present invention includes apertures within the device for containing the bioactive material. This embodiment is illustrated in FIGS. 8, 9, 10A, 10B, 10C and 10D. FIG. 8 shows an arm of the stent of FIG. 7 wherein the arm includes holes 28 into which a bioactive material is contained. FIG. 9 shows a section of the arm of the stent along lines 9—9 of FIG. 8. Bioactive material 18 is contained within the hole 28 where the base material 14 contains coating 16 and further where porous layer 20 forms the outer most layer for the bioactive material 18 to diffuse through. In an alternative embodiment, wells 28' may be cut, etched or stamped into the base material 14 of the device in which a bioactive material 18 may be contained. This embodiment is illustrated in FIGS. 10A, 10B, 10C and 10D which are sectional FIGs. taken along line 10—10 of FIG. 8. The wells 28' may also be in the form of slots or grooves in the surface of the base material 14 of the medical device. This aspect of the invention provides the advantage of better controlling the total amount of the bioactive material 18 to be released as well as the rate at which it is released. For example, a V-shape well 28', as illustrated in FIG. 10D, will contain less quantity of bioactive material 18 and release the material at geometric rate as compared to a square shaped well 28', as illustrated in FIG. 10B, which will have a more uniform, linear release rate.

The holes, wells, slots, grooves and the like, described above, may be formed in the surface of the device 10 by a variety of techniques. For example, such techniques include drilling or cutting by utilizing lasers, electron-beam machining and the like or employing photo resist procedures and etching the desired apertures.

All the bioactive materials discussed above that may be coated on the surface of the device 10 may be used to be contained within the apertures of this aspect of the invention. Likewise, layers of bioactive materials and porous layers may be applied and built up on the exterior surfaces of the device as described previously with regard to other aspects of the invention, e.g., heparin, may be covalently bound to one surface of the device illustrated in FIG. 9.

The method of making the device 10 according to the present invention may now be understood. In its simplest form, the method comprises the steps of depositing the at least one layer 18 of bioactive material over the structure 12, followed by depositing the at least one porous layer 20, preferably by vapor deposition or plasma deposition, over the at least one bioactive material layer 18 on the one surface of structure 12. The at least one porous layer 20 being composed of a biocompatible polymer and being of a thickness adequate to provide a controlled release of the bioactive material. Preferably, the at least one additional coating layer 16 is first posited by vapor deposition directly on the base material 14 of the structure 12. Such deposition is carried out by preparing or obtaining di-p-xylylene or a derivative thereof, sublimating and cracking the di-p-xylylene or derivative to yield monomeric p-xylylene or a monomeric derivative, and allowing the monomer to simultaneously condense on and polymerize over the base material 14. The deposition step is carried out under vacuum, and the base material 14 maintained at or near room temperature during the deposition step. The deposition is carried out in the absence of any solvent or catalyst for the polymer, and in the absence of any other action to aid polymerization. One preferred derivative for carrying out the deposition step is dichloro-di-p-xylylene. The parylene or parylene derivative is preferably applied at the thickness disclosed above, to yield a coating layer 16 which is substantially nonporous, but in any event less porous than the at least one porous layer 20 to be applied. If required by the composition of the coating layer 16, the layer 16 is then surface processed in an appropriate manner, for example, by plasma treatment as disclosed above.

The at least one layer 18 of the desired bioactive material or materials is then applied to the one surface of the structure 12, and in particular, onto the additional coating layer 16. This application step can be carried out in any of a variety of convenient ways, such as by dipping, rolling, brushing or spraying a fluid mixture of the bioactive material onto the additional coating layer 16, or by electrostatic deposition of either a fluid mixture or dry powder of the bioactive material, or by any other appropriate method. Different bioactive agents may be applied to different sections or surfaces of the device.

It can be particularly convenient to apply a mixture of the bioactive material or materials and a volatile fluid over the structure, and then remove the fluid in any suitable way, for example, by allowing it to evaporate. When heparin and/or dexamethasone or its derivatives serve as the bioactive material(s), the fluid is preferably ethyl alcohol. The bioactive material is preferably applied in an amount as disclosed above.

Other methods of depositing the bioactive material layer 18 over the structure 12 would be equally useful. Without regard to the method of application, however, what is important is that the bioactive material need only be physically held in place until the porous layer 20 is deposited over it. This can avoid the use of carriers, surfactants, chemical binding and other such methods often employed to hold a bioactive agent on other devices. The additives used in such methods may be toxic, or the additives or methods may alter or degrade the bioactive agent, rendering it less effective, or even toxic itself. Nonetheless, if desired these other methods may also be employed to deposit the bioactive material layer 18 of the present invention.

The bioactive material may, of course, be deposited on the one surface of the structure 12 as a smooth film or as a layer of particles. Moreover, multiple but different bioactive materials may be deposited in a manner that different surfaces of the device contain the different bioactive agents. In the latter case, the particle size may affect the properties or characteristics of the device 10, such as the smoothness of the uppermost porous coating 20, the profile of the device 10, the surface area over which the bioactive material layer 18 is disposed, the release rate of the bioactive material, the formation of bumps or irregularities in the bioactive material layer 18, the uniformity and strength of adhesion of the bioactive material layer 18, and other properties or characteristics. For example, it has been useful to employ micronized bioactive materials, that is, materials which have been processed to a small particle size, typically less than 10 $\mu$m in diameter. However, the bioactive material may also be deposited as microencapsulated particles, dispersed in liposomes, adsorbed onto or absorbed into small carrier particles, or the like.

In still another embodiment according to the present invention, the bioactive material may be posited on the one surface of structure 12 in a specific geometric pattern. For example, the tips or arms of a stent may be free of bioactive material, or the bioactive material may be applied in parallel lines, particularly where two or more bioactive materials are applied to the same surface.

In any event, once the bioactive material layer 18 is in place, the at least one porous layer 20 is then applied over the at least one bioactive material layer 18 in the same manner as for the application of the at least one additional coating 16. A polymer such as parylene or a parylene derivative is applied at the lesser thickness disclosed above, however, so as to yield the at least one porous layer 20.

Any other layers, such as the second bioactive material layer 22 or the additional porous layer 24, are applied in the appropriate order and in the same manner as disclosed above. The steps of the method are preferably carried out with any of the bioactive materials, structures, and base materials disclosed above.

Of course, polyimide may be deposited as any or all of the porous and additional coating layers 20, 24 and/or 16 by vapor deposition in a manner similar to that disclosed above for parylene and its derivatives. Techniques for the plasma deposition of polymers such as poly(ethylene oxide), poly (ethylene glycol), poly(propylene oxide), silicone, or a polymer of methane, tetrafluoroethylene or tetramethyl-disiloxane on other objects are well-known, and these techniques may be useful in the practice of the present invention.

Another technique for controlling the release of the bioactive material may include depositing monodispersed polymeric particles, i.e., referred to as porogens, on the surface of the device 10 comprising one or more bioactive materials prior to deposition of porous layer 20. After the porous layer 20 is deposited and cured, the porogens may be dissolved away with the appropriate solvent, leaving a cavity or pore in the outer coating to facilitate the passage of the underlying bioactive materials.

The method of using the device 10 of the present invention in medically treating a human or veterinary patient can now be easily understood as well. The method of the present invention is an improvement over previous methods which include the step of inserting into a patient an implantable vascular device 10, the device 10 comprising a structure 12 adapted for introduction into the vascular system of a patient, and the structure 12 being composed of a base material 14. The method according to the present invention comprises the preliminary steps of depositing at least one layer 18 of a bioactive material on one surface of the structure 12, followed by depositing at least one porous layer 20 over the at least one bioactive material layer 18, the porous layer 20 being composed of a polymer and having a thickness adequate to provide a controlled release of the bioactive material when the device 10 is positioned in the patient's vascular system.

The method can further entail carrying out the two depositing steps with the various embodiments of the device 10 disclosed above, in accordance with the method of making the device 10 disclosed above. More particularly, the step of depositing the at least one porous layer 20 can comprise polymerizing the at least one layer 20 from a monomer vapor, preferably a vapor of parylene or a parylene derivative, free of any solvent or catalyst. The method can also comprise the step of depositing the at least one additional coating layer 16 between the structure 12 and the at least one bioactive material layer 18.

The method of treatment according to the present invention is completed by inserting the device 10 into the vascular system of the patient. The at least one porous layer 20 and any additional porous layers 24 automatically release the bioactive material or materials in a controlled fashion into the patient.

The remaining details of the method of medical treatment are the same as those disclosed with respect to the method of making the device 10 of the present invention; for the sake of brevity, they need not be repeated here.

In view of the disclosure above, it is clear that the present invention provides an implantable medical device which achieves precise control over the release of one or more bioactive materials contained in the device. Moreover, the polyimide, parylene, parylene derivative or other polymeric layers 16, 20 and/or 24 can be remarkably thin, in comparison to the thicknesses required for other polymer layers. The bulk or substantial majority of the overall coating on the structure 12 can therefore consist of bioactive material. This allows the supply of relatively large quantities of bioactive material to the patient, much greater than the amounts supplied by prior devices. These quantities of bioactive material can be supplied to any of a wide variety of locations within a patient during or after the performance of a medical procedure, but are especially useful for preventing abrupt closure and/or restenosis of a blood vessel by the delivery of an antithrombic or other medication to the region of it which has been opened by PTA. The invention permits the release rate of a bioactive material to be carefully controlled over both the short and long terms. Most importantly, any degradation of the bioactive material which might otherwise occur by other polymer coating techniques is avoided.

The other details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of ordinary skills in this area, in view of the present disclosure.

Furthermore and advantageously, silver can be used alone, as a coating, in combination with other carrier, drug or medicament materials, as one of several other layers of materials, and with base materials that are used to improve the adhesion of silver to any other carrier, drug, medicament or base material. Advantageously, silver may be ion beam bombarded or implanted to provide a specific surface energy density in the preferred range of 20 to 30 dynes per centimeter. In this particular range, not only is the antiproliferative effect of the stent or device enhanced but the outer surface of the stent or device is resistant to the formation of thrombus, fungus, bacteria, and encrustations thereon. Silver coatings, implantations, impregnations or dispersions having a thickness in the range of about $1 \times 10^{-5}$ cm to about $1.5 \times 10^{-2}$ cm, preferably in the range of about $3 \times 10^{-5}$ cm to about $1.25 \times 10^{-2}$ cm and most preferably a thickness of about $3 \times 10^{-5}$ cm are contemplated dependent on the thickness of the base material or intermediate layers thereon. The silver, silver alloys, or silver ions may be deposited as a continuous layer on the base material or on a coating over the base material. Alternatively, the silver, silver ions and/or silver alloys may be implanted or impregnated into the surface matrix of the base material or a coating on the base material. Stents or other implantable medical devices using a base material with a silver coating deposited directly thereon is one example of a coating configuration. Another configuration of the stent is to include a base material with a coating of a carrier or dispersant material such as parylene positioned thereon or therein along with a coating, deposition, impregnation, or implantation and the like thereon is also contemplated. Another configuration of the silver stent can include a base material with alternating layers of a carrier material, silver, drug or medicament is also contemplated. Various recesses or cavities included in the surface or made part of the stent or implantable medical device are also contemplated and included with the silver device. It should be recognized that above described methods and thicknesses of deposited and/or implanted silver, silver ions and/or silver alloys will result in a bioactive effective amount of silver. Depicted in FIG. 11 is endovascular stent 29, which is commercially known as the Gianturco-Roubin I and available from Cook Incorporated, Bloomington, Indiana. This stent is described in detail in U.S. Pat. No. 4,907,336, which is incorporated herein by reference in its entirety. Endovascular stent 29 is a balloon expandable stent and is formed from a single strand of cylindrical stainless steel wire 33 having a wire diameter 30 in the range of 0.002 inches to 0.030 inches. The typical wire diameter of the stent is 0.010 inches. The stent is shown in an expanded condition which can range in overall diameter 31 from 2 to 20 mm with a typical diameter of 4 mm. The overall length 32 of the stent is in the range of 10 to 60 mm with a typical length of 25 mm.

FIG. 12 depicts an enlarged cross-sectional view of stent wire 33 of stent 29 of FIG. 11. Stent wire 33 is formed of a base material such as medical grade stainless steel 34 with carrier layer 35 of for example parylene and a layer of silver 36 deposited there over. The silver coating layer 36 is applied using a Spi-Argent process commercially available from the Spire Corporation of Bedford, Mass. Providing the stent wire with a particular surface energy density such as, for example, in the 20 to 30 dyne per centimeter range is described in U.S. Pat. No. 5,289,831 which is incorporated herein by reference in its entirety.

Alternatively, stent wire 33 can include a base material of, for example, stainless steel with the silver layer deposited directly on the outer surface of the base material. The stainless steel wire with silver thereon is deposited using an electroplating process. This is only one of several deposition or plating processes contemplated. Vapor deposition, sputtering or ion beam deposition or implantation is also contemplated. A base material of tantalum, copper, or any of the herein described polymer or copolymer materials are also included. The stent base material is then silver coated or alternatively, ion beam bombarded. The base material can also include a 50/50 mixture of silver and copper. Silver bearing solder of, for example, 70% silver, 15% copper, and 15% zinc can also be applied to one of the contemplated base materials to supplement the antiproliferative effect.

In a second alternative embodiment, the stent wire can be made of pure silver.

FIG. 13 depicts stent 29 of FIG. 11 in a collapsed arrangement around balloon 37 of balloon catheter 38.

FIG. 14 depicts stent 29 of FIG. 13 in an expanded condition after delivery balloon 27 has been inflated by, for example, an attending physician.

FIG. 15 depicts another embodiment of silver implantable vascular stent 39. The base material of the stent is known as the Gianturco-Roubin II vascular stent available through Cook Incorporated of Bloomington, Indiana. This stent is typically etched from a flat sheet of material such as stainless steel or any other of the base materials described herein. This balloon expandable stent is described in U.S. patent application Ser. No. 08/378,073 filed Jan. 25, 1995 which has been allowed by the U.S. Patent and Trademark Office. In a first configuration, this balloon expandable stent 39 is formed of pure silver having a thickness in the range of 0.002 inches to 0.015 inches with a typical thickness in the range of 0.003 inches to 0.006 inches. The waveform legs 40 have a width of approximately 0.003 inches to 0.030 inches. Although shown in the collapsed position, the overall diameter 41 in the expanded position is 2 to 20 mm having a typical diameter of 4 mm. The overall length 42 of stent 39 is in the range of 10 to 60 mm with a typical length of 25 mm. Stent 39 includes radiopaque marker of, for example, gold positioned at the end of longitudinal reinforcing member 43. The sheet from which stent 39 is etched is formed from the following base materials, coatings, medicants, drug and/or carrier materials. In one configuration, the sheet is formed from pure silver. In a second configuration the sheet is formed with a base material of stainless steel with silver electroplated thereon. Ion beam deposition, sputtering or other ion beam deposition techniques are contemplated when the plating thickness approximates the 3,000 Angstrom thickness. This second configuration is depicted in FIG. 16 in which a cross-sectional view is provided of waveform leg 40. Base material 44 of, for example, silver is shown with a layer or coating of silver 45 deposited thereon.

In a third configuration of stent 39, the stent is etched from a base material of, for example, stainless steel or other base materials described herein. FIG. 17 depicts a cross-sectional view of waveform leg 40 with base material 44 with carrier layer 46 and silver layer 45 deposited over the carrier and base layers. Parylene carrier layer 46 is applied, for example, using the SpiArgent process as previously described. Although the base material has been previously described as preferably stainless steel, tantalum as well as any of the polymer or copolymer materials are also contemplated.

In a fourth configuration of stent 39 the stent is etched from a base material 44 as previously described or contemplated. Deposited on base material 44 of waveform leg 40 are alternating layers of silver 45 and intermediate layers 47 and 48 of, for example, carrier materials such as parylene, drug or medicament materials as previously described herein. Recesses or coatings can be applied as depicted in previously described FIGS. 1–10D. In this manner, various combinations of effectiveness of antiproliferative silver can be used in combination with other materials to provide desired combinational effects.

Figure 19:
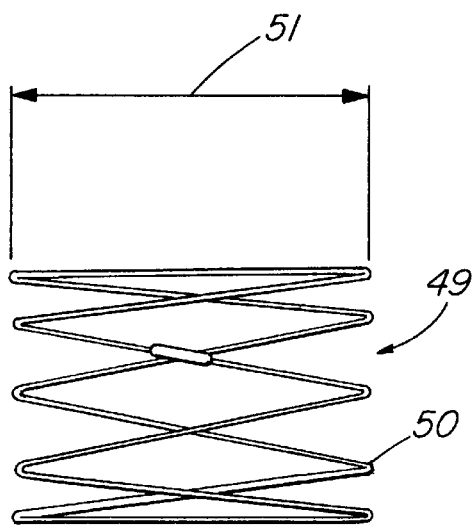
FIG. 19 depicts a side view of another embodiment of a self-expanding, silver "Z" endovascular stent.

FIG. 19 depicts a side view of self-expanding endovascular stent 49 commonly referred to a "Z" stent commercially available from Cook Incorporated of Bloomington, Ind. This stent is fully described in U.S. Pat. No. 4,580,568 which is incorporated herein by reference in its entirety. This self-expanding stent is formed from cylindrical wire 50 and bent into a zig-zag pattern and into a tubular form. Wire 50 has a wire diameter in the range of 0.004 inches to 0.020 inches with a typical diameter of 0.012 inches. The overall length 51 of Z stent 49 ranges from 2 to 5 cm with a typical length of 2.5 cm.

Figure 20:
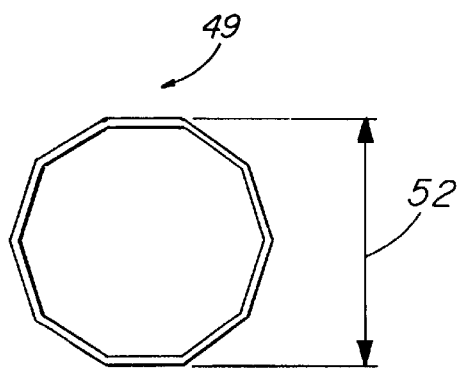
FIG. 20 depicts an end view of the Z stent of FIG. 19.

FIG. 20 depicts an end view of Z stent 49 of FIG. 19. The tubular configuration of this Z stent is shown with an outer diameter 52 in the range of 5 to 40 mm with a typical 12 mm diameter.

Figure 21:
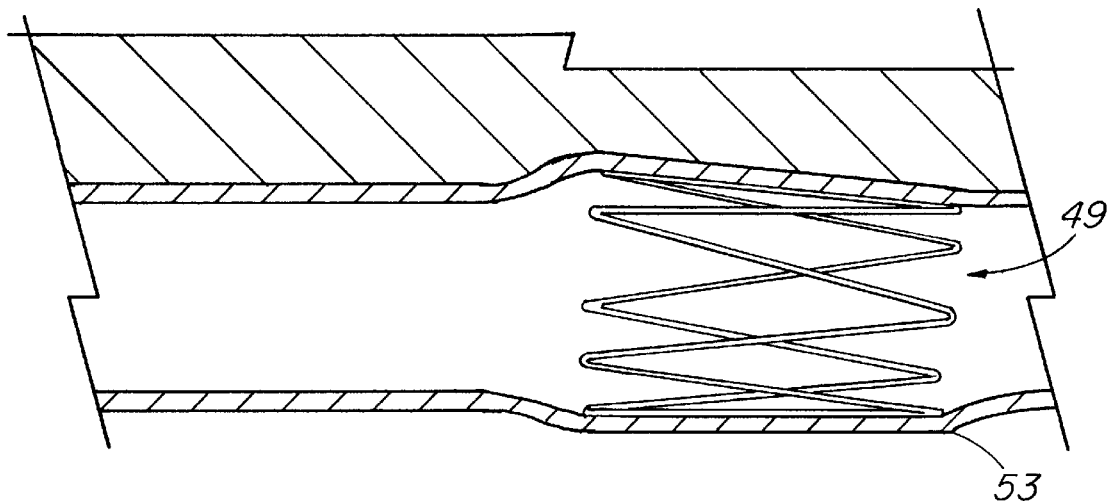
FIG. 21 depicts the Z stent of FIG. 19 deployed in a blood vessel.

FIG. 21 depicts Z stent 49 of FIG. 19 in blood vessel 53. The base material of this self-expanding stent comprises, for example, a spring temper stainless steel such as series 304 or 316 plated with silver as previously described. Alternative layers of carrier material along with drugs or medicants are also contemplated as previously described. The base material can also comprise a nickel-titanium alloy such as Nitinol which is available from the Raychem Corporation of Menlo Park, California.

Figure 22:
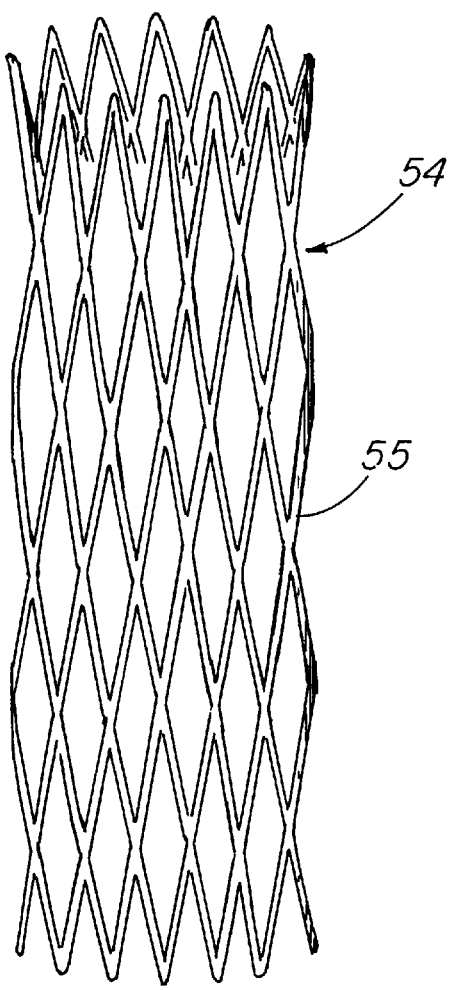
FIG. 22 depicts a balloon expandable, silver stent formed from a cylindrical tube.

FIG. 22 depicts another embodiment of endovascular stent 54 which is described in detail in U.S. Pat. No. 4,733,665 and Reexamination Certificate B1 U.S. Pat. No. 4,773,665. Reference to this patent is incorporated herein in it entirety. Stent 54 is typically formed from a tube of stainless steel material with a plurality of slits 55 cut in the tubular wall. This stent is delivered on a balloon catheter and expanded at the desired vascular site. The base materials, silver plating and/or carrier, drug or medicament materials are also contemplated as previously described.

Industrial Applicability

The present invention is useful in the performance of vascular surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts. It is contemplated that only part of a device need be coated. Furthermore, different parts of the device can be coated with different bioactive materials or coating layers. It is also contemplated that different sides or regions of the same part of a device can be coated with different bioactive materials or coating layers.

What is claimed is:

1. An implantable medical device (10), comprising:
    a structure (12) adapted for introduction into a patient, the structure (12) being composed of a base material (14);
    at least one layer (18) of a bioactive material posited on at least one surface of the structure (12);
    at least one porous layer (20) posited over the layer (18) of bioactive material and composed of a polymer to provide for a controlled release of the bioactive material therethrough; and
    an antiproliferative agent selected from the group consisting of elemental silver, silver alloys, silver ions and other silver containing materials and included in or on at least one of said base material, said bioactive material, and said polymer.

2. The device (10) according to claim 1, wherein the at least one porous layer (20) is one polymerized from a catalyst-free monomer vapor.

3. The device (10) according to claim 1, wherein the polymer is selected from the group consisting of a polyamide, polymers of parylene or derivatives thereof, poly(ethylene oxide), poly(ethylene glycol), poly(propylene oxide), silicone based polymers, polymers of methane, tetrafluoroethylene or tetramethyldisiloxane or a polymer derived from photopolymerizeable monomers.

4. The device (10) according to claim 3, wherein the thickness of the at least one porous layer (20) is about 5,000 to 250,000 Å.

5. The device (10) according to claim 1, further comprising at least one additional coating layer (16) between the structure (12) and the at least one bioactive material layer (18).

6. The device (10) according to claim 5, wherein the at least one additional coating layer (16) is less porous than the at least one porous layer (20).

7. The device (10) according to claim 6, wherein the polymer is selected from the group consisting of polyamide, polymers of parylene or derivatives thereof, or a polymer derived from photopolymerizable monomers of bisphenol A diglycidyl ether and acrylic acid or methacrylic acid, and the at least one additional coating layer (16) is about 50,000 to 500,000 Å thick.

8. The device (10) according to claim 1, wherein the structure (12) is configured as a vascular stent.

9. The device (10) according to claim 1, wherein the structure (12) is configured as at least one of: a stent, a vascular or other graft, a vascular or other graft in combination with a stent, heart valve, an orthopedic device, appliance, implant or replacement, or portion thereof; or a portion of any of these.

10. The device (10) according to claim 1, wherein the base material (14) is biocompatible.

11. The device (10) according to claim 10, wherein the base material (14) of the structure (12) includes at least one of: stainless steel, tantalum, titanium, Nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers thereof; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a mixture thereof.

12. The device (10) according to claim 1, wherein the bioactive material includes at least one of: heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, Taxol® or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiogenin, angiopeptin (a growth hormone antagonist), a growth factor or an anti-growth factor antibody, or another growth factor antagonist; dopamine, bromocriptine mesylate, pergolide mesylate or another dopamine agonist; $^{60}$Co, $^{192}$Ir, $^{32}$P, $^{111}$In, $^{90}$Y, $^{99m}$Tc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C-, $^{3}$H-, $^{131}$I-, $^{32}$P— or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs, or a mixture of any of these.

13. The device (10) according to claim 1, wherein the structure (12) has a gross surface area, and wherein the at least one layer (18) of bioactive material contains about 0.01 to about 4 mg of the bioactive material per cm$^2$ of the gross surface area of the structure (12).

14. The device (10) according to claim 1, wherein the structure (12) includes different surfaces, and wherein different bioactive materials are posited on the different surfaces of the structure (12).

15. The device (10) according to claim 1, wherein the layer (18) of bioactive material is posited on one surface of the structure (12) and thereby defines a bioactive-material-free surface of the structure (12) different from the one surface of the structure (12), the porous layer (20) is posited over the layer (18) of bioactive material on the one surface of the structure (12) and over the bioactive-material-free surface of the structure (12), and a second bioactive material is posited on the porous layer (20) and forms an outermost layer for the device (10).

16. The device (10) according to claim 15, wherein a different and third bioactive material is posited on the bioactive-material-free surface of the structure (12), the porous layer (20) being posited over the first-mentioned bioactive material and the third bioactive material; and wherein the second bioactive material forming the outermost layer for the device (10) is covalent heparin bound to the porous layer (20).

17. The device (10) according to claim 1, wherein the structure (12) includes a plurality of different surfaces, and wherein the device (10) comprises either a single bioactive material on one of the different surfaces of the structure (12), or a plurality of different bioactive materials on the different surfaces of the structure (12) with the porous layer (20) over said bioactive material or materials so that a second of the plurality of bioactive materials forms an outermost layer of the device (10) over the porous layer (12).

18. The device (10) according to claim 1, wherein the structure (12) has a plurality of different surfaces, and wherein individual ones of a plurality of layers of different bioactive materials are posited on the different surfaces of the structure (12) with the provisos that (a) the same bioactive material is not posited on different surfaces of the structure (12) within the same individual one of the plurality of different layers of bioactive materials, and (b) either a porous layer or a bioactive material layer may form an outermost layer for the device (10).

19. The device according to claim 5, wherein a highly pure elemental silver layer having a uniform thickness is posited on the at least one porous layer (20).

20. The device according to claim 1, wherein the polymer composing the at least one porous layer (20) forms a matrix having highly pure elemental silver, silver ions or a combination thereof impregnated therein.

21. The device according to claim 1, wherein said device is a balloon expandable vascular stent.

22. The device according to claim 1, wherein said device is a self-expanding vascular stent.

23. The device (10) according to claim 6, wherein the at least one additional coating layer (16) is composed of the same polymer as the at least one porous layer (20).

24. The device (10) according to claim 6, wherein the at least one additional coating layer (16) is composed of a different polymer than the at least one porous layer (20).

25. An implantable medical device (10), comprising:
- a structure (12) adapted for introduction into a patient, the structure (12) being composed of a base material (14);
- at least one layer (18) of a bioactive material posited on at least one surface of the structure (12);
- at least one porous layer (20) posited over the layer (18) of bioactive material and composed of a polymer to provide for a controlled release of the bioactive material therethrough;
- an antiproliferative agent selected from the group consisting of elemental silver, silver alloys, silver ions and other silver containing materials and included in or on at least one of said base material, said bioactive material, and said polymer; and
- at least one additional coating layer (16) between the structure (12) and the at least one bioactive material layer (18);
- wherein the at least one additional coating layer (16) is less porous than the at least one porous layer (20).

26. The device (10) according to claim 25, wherein the polymer is selected from the group consisting of polyamide, polymers of parylene or derivatives thereof, or a polymer derived from photopolymerizable monomers of bisphenol A diglycidyl ether and acrylic acid or methacrylic acid, and the at least one additional coating layer (16) is about 50,000 to 500,000 Å thick.

27. The device (10) according to claim 25, wherein the at least one additional coating layer (16) is composed of the same polymer as the at least one porous layer (20).

28. The device (10) according to claim 25, wherein the at least one additional coating layer (16) is composed of a different polymer than the at least one porous layer (20).

* * * * *